United States Patent
Eismann et al.

(10) Patent No.: US 11,852,758 B2
(45) Date of Patent: Dec. 26, 2023

(54) METHOD FOR OPERATING A DIRECTLY-CONVERTING X-RAY DETECTOR, X-RAY DETECTOR AND IMAGING X-RAY DEVICE

(71) Applicant: Siemens Healthcare GmbH, Erlangen (DE)

(72) Inventors: Alfons Eismann, Pinzberg (DE); Ulrich Wiesmann, Erlangen (DE); Andreas Urban, Bayern (DE)

(73) Assignee: SIEMENS HEALTHCARE GMBH, Erlangen (DE)

( * ) Notice: Subject to any disclaimer, the term of this patent is extended or adjusted under 35 U.S.C. 154(b) by 0 days.

(21) Appl. No.: 17/844,892

(22) Filed: Jun. 21, 2022

(65) Prior Publication Data
US 2022/0413168 A1 Dec. 29, 2022

(30) Foreign Application Priority Data
Jun. 23, 2021 (DE) ...................... 10 2021 206 501.5

(51) Int. Cl.
*G01T 1/17* (2006.01)
(52) U.S. Cl.
CPC ...................................... *G01T 1/17* (2013.01)
(58) Field of Classification Search
CPC ..................................................... G01T 1/17
See application file for complete search history.

(56) References Cited

U.S. PATENT DOCUMENTS

| | | |
|---|---|---|
| 2003/0016779 A1 | 1/2003 | Pohan et al. |
| 2003/0043959 A1 | 3/2003 | Wischmann et al. |
| 2005/0105687 A1 | 5/2005 | Heismann et al. |

(Continued)

FOREIGN PATENT DOCUMENTS

| | | |
|---|---|---|
| CN | 1752881 A | 3/2006 |
| CN | 101133961 A | 3/2008 |

(Continued)

OTHER PUBLICATIONS

German Office Action and English translation thereof dated Feb. 22, 2022.

(Continued)

*Primary Examiner* — Hugh Maupin
(74) *Attorney, Agent, or Firm* — Harness, Dickey & Pierce, P.L.C.

(57) ABSTRACT

A directly-converting X-ray detector includes: a directly-converting sensor material, which is to be maintained at a working temperature, and configured to have a DC voltage applied thereto; a conditioning unit configured to cause a base current to flow through the sensor material; a heating unit for the sensor material, the heating unit configured to be regulated by a regulating unit to maintain the working temperature; and a control device having a plurality of electronics units, which include the regulating unit. When a new configuration and/or a reconfiguration process takes place, the control device is configured to maintain the operation of the conditioning unit, and to interrupt the operation of the heating unit and/or maintain the operation of the heating unit with the control value most recently ascertained in ordinary operation of the regulating unit.

20 Claims, 2 Drawing Sheets

(56) References Cited

U.S. PATENT DOCUMENTS

| | | | |
|---|---|---|---|
| 2007/0158575 A1* | 7/2007 | Heismann | G01K 7/01 |
| | | | 250/370.15 |
| 2008/0054182 A1 | 3/2008 | Yokoyama et al. | |
| 2013/0248729 A1 | 9/2013 | Hannemann et al. | |
| 2013/0279648 A1 | 10/2013 | Joshi et al. | |
| 2015/0212215 A1* | 7/2015 | Goderer | G01T 1/244 |
| | | | 250/370.15 |
| 2017/0176608 A1 | 6/2017 | Ergler et al. | |
| 2017/0192110 A1* | 7/2017 | Steadman Booker | |
| | | | A61B 6/4488 |
| 2018/0097515 A1* | 4/2018 | Norling | H03K 17/0828 |
| 2018/0338736 A1 | 11/2018 | Ergler et al. | |
| 2021/0318255 A1* | 10/2021 | Hardman | G01K 13/00 |
| 2022/0035053 A1* | 2/2022 | Takano | G01R 33/0354 |

FOREIGN PATENT DOCUMENTS

| | | |
|---|---|---|
| CN | 103365314 A | 10/2013 |
| DE | 10139234 A1 | 2/2003 |
| DE | 10212638 A1 | 10/2003 |
| DE | 102014201741 A1 | 8/2015 |
| DE | 102014207324 A1 | 10/2015 |
| DE | 102015225774 B3 | 6/2017 |
| DE | 102017208955 A1 | 11/2018 |

OTHER PUBLICATIONS

German Decision to Grant and English translation thereof dated Aug. 22, 2022.

\* cited by examiner

METHOD FOR OPERATING A DIRECTLY-CONVERTING X-RAY DETECTOR, X-RAY DETECTOR AND IMAGING X-RAY DEVICE

CROSS-REFERENCE TO RELATED APPLICATION(S)

The present application claims priority under 35 U.S.C. § 119 to German Patent Application No. DE 10 2021 206 501.5, filed Jun. 23, 2021, the entire contents of which are incorporated herein by reference.

FIELD

Embodiments of the present invention relate to a method for operating a directly-converting, in particular photon-counting, X-ray detector, wherein the X-ray detector comprises: a directly-converting sensor material which is to be kept at a working temperature and to which a DC voltage is applied, a conditioning unit causing a base current to flow through the sensor material, a heating unit for the sensor material, regulated by a regulating unit to maintain the working temperature, and a control device having a plurality of electronics units comprising the regulating unit. Embodiments of the present invention additionally relate to an X-ray detector and an imaging X-ray device.

BACKGROUND

X-ray imaging represents, particularly in the medical field, a long-used advantageous investigative tool. Current research efforts are directed to the use of directly-converting X-ray detectors, in particular as photon-counting X-ray detectors. As distinct from X-ray detectors in which firstly, incident X-ray photons generate secondary light in a scintillator which is then measured, in the case of direct conversion, a conversion of X-ray radiation into charge carriers directly is aimed for, the flow of which (that is, the current) can then be measured. Directly-converting X-ray detectors or X-ray sensors are based upon the absorption of X-ray radiation in a sensor material, specifically a semiconductor, which results in the generation of electron-hole pairs. If large DC voltages are applied, the charge carriers can be evaluated separately and the resulting current pulse can subsequently be evaluated with suitable electronics.

Exemplary, directly-converting X-ray detectors are described in DE 10 2014 207 324 A1 and in DE 10 212 638 A1.

Exemplary, promising sensor materials comprise cadmium telluride and cadmium zinc telluride (CdTe and CdZnTe, abbreviated to CZT). A DC voltage, typically a high voltage, is applied to the sensor material in order to create a current flow through the sensor material during X-ray irradiation, which is evaluated by the, in particular directly connected, electronics. This means that when X-ray radiation is incident thereon, as described, charge carriers (electron-hole pairs) and via the sensor material to which the high voltage is applied, a current flows. In this context, it is known, for example for the avoidance of drift effects, to provide a conditioning unit for the sensor material, which ensures the presence of a particular base current through the sensor material. A conditioning unit of this type can be based, for example, upon an illumination of the sensor material, in particular with infrared (IR) light.

However, currents, in this case the base current and the measuring current, through the sensor material also lead to heating of the sensor material. It has therein been found in current investigations that temperature differences in the sensor material lead to unwanted drift properties, as a result of which, in particular in medical imaging, unwanted image artifacts can arise in an X-ray image recorded with the X-ray detector. It has therefore been proposed to keep the temperature of the sensor material in a stable state, thus in particular at a pre-determined working temperature. The working temperature can be, for example, between 30° C. and 50° C., in particular 40° C.

In order to achieve this, in addition to the conditioning unit which passes a certain amount of "base current" through the sensor material, a so-called sensor material heater can be used which "preheats" the sensor material and, for this purpose comprises, for example, a heating unit which is operated controlled by a regulating unit. If particular electronics units are present, for example application-specific integrated circuits (ASICs) utilized as measuring units, their dissipation power can be emitted to the sensor material as heat.

Otherwise expressed, two basic and one optional heat source are available for the sensor material. Firstly, a heat input is provided by the constantly active conditioning unit which feeds in a certain base current. The sensor material heater can provide, for example on the basis of temperature measurement values from temperature sensors and/or other input variables, a heat input which is lowered, in particular during the X-ray input in order to compensate for the temperature increase through the X-ray radiation. Finally, electronics units connected directly to the sensor material optionally also exist, in particular measuring units such as ASICs which provide a dissipation power and thereby heat which passes, through heat conduction, into the sensor material. This heat source also normally exists continuously, since the corresponding electronics units are permanently active. In particular with regard to a so-called "always on" operation, which is intended to prevent a slow reheating of the sensor material, there exists the requirement that these units of the control device of the X-ray detector should not be switched off. This applies also for the sensor material heater.

SUMMARY

It can occur for a variety of reasons that the control device of the X-ray detector must be newly configured or reconfigured. For example, this can involve a maintenance operation, in particular, an updating of the X-ray device containing the X-ray detector but it is also conceivable that, for example, due to the penetration of X-ray radiation into an electronics unit of the control device, a new configuration (reconfiguration) must take place. In such cases, the different units of the control device, thus in particular the electronics units on the front-end modules, are deactivated so that a drifting off of the temperature of the sensor material occurs, and therefore the disadvantageous drift properties of the X-ray detector come to light.

It has been recognized, in particular, that after such a new configuration or reconfiguration of the electronics, which occurs relatively often for system-related reasons, for example for updates, service intervals and the like, it is necessary to wait for up to 24 hours until a stable function for a flawless image quality of the X-ray device containing the X-ray detector is available again.

In this regard it should be noted in particular that even with deactivation times of only a few seconds, negative effects with regard to the image quality and image artifacts can occur since the working temperature of the sensor material is no longer assured. Initialization processes for electronics in known computed tomography devices are based, for example, upon particular charging chains and last for in the region of 30-60 seconds. During this time, electronics units of the control device of the central unit of the computed tomography device are not reachable/controllable and/or are unpowered and cannot cause any heat input into the sensor material. Even this period is long enough not to be able to preclude image artifacts on subsequent immediate resumption of operation.

It is therefore the object of embodiments of the present invention to reduce outage times of directly-converting X-ray detectors due to deviations of the predetermined tempering of the sensor material.

In order to achieve this object, in a method of the type mentioned in the introduction, it is provided that, by way of the control device, when a new configuration and/or a reconfiguration process takes place the operation of the conditioning unit is maintained, and only during an actual configuration time of the regulating unit, in particular for a period shorter than a second, either the operation of the heating unit is interrupted and/or the operation of the heating unit is maintained with the control value most recently ascertained in ordinary operation of the regulating unit.

Therefore circuit-based measures are proposed in order to keep the sensor material as accurately as possible at the predetermined working temperature in order as far as possible to prevent outage times of the X-ray detector and thus to be able to provide an at least approximately "always on" operation. The conditioning unit which provides, for example, by illuminating the sensor material to which a (high) DC voltage is applied, the base current in the sensor material is typically set during the first commissioning to at least one corresponding operating parameter that typically no longer changes during the subsequent operation. Therefore, the at least one operating parameter of the conditioning unit represents a constant value that must be held in a storage of the control device; only during service usage and/or on a renewed tuning of the X-ray device containing the directly-converting X-ray detector, it can be provided that the at least one operating parameter is set anew, after which it again remains constant. This fact makes it possible, even during a reconfiguration and/or new configuration in the control device to leave the conditioning unit active in a targeted way with a circuit-based measure, which means that during a configuration of the electronics, the circuit element forming the conditioning unit is not influenced and is still kept active. Thus, the heat component that is provided to the sensor material by the conditioning unit remains constant during a new configuration and/or reconfiguration process, which contributes to the temperature maintenance in the sensor material.

In addition, it is proposed to deactivate the heating unit of the sensor material heater that is formed by the combination of heating unit and regulating unit, if at all, then only for the minimum necessary time period, or even to continue to operate it with the last ascertained control value during ordinary operation, that is normal operation, of the regulating unit during the new configuration of the regulating unit. Therein, in the context of embodiments of the present invention, as will be explained in greater detail, configuration methods are used which preferably require a configuration timespan of less than one second, in particular of only a few hundred milliseconds. Since the thermal mass of the sensor material and/or of the X-ray detector is per se, exactly like thermal time constants, sufficiently large, these short timespans of less than a second in which the heating unit is switched off and/or is continuously further operated unregulated, these short timespans are not crucial, in particular not such that it would become visible in the image quality, as experiments have shown. At the same time, however, an uncontrolled state of the sensor material heater is prevented by way of the regulation algorithm. In particular with control systems that are designed to be highly dynamic, which for example provide large control values for rapid heating in a short time, it can therefore be more suitable to deactivate the heating unit since an "overheating" is then prevented—in particular if a plurality of configuration attempts are needed—since due to the thermal inertia in the short configuration timespan, the temperature loss is still kept within limits.

In this context, it can otherwise also be provided that the last ascertained control value is kept available in a storage of the control device and, on a restart of ordinary operation of the regulating unit after the configuration time, is used as a starting value for the control value. In this way, an improved transition can be achieved between the closed-loop control before and after the reconfiguration or the new configuration, without a completely new adjustment being necessary. If relevant, a control history can also be stored, where this is provided for.

In a particularly advantageous, specific configuration of embodiments of the present invention, it can be provided that the configuration of the regulating unit takes place via a serial configuration line which is connected to a configuration interface of the regulating unit. Via such a serial configuration line which leads, for example, to all the configuration interfaces of the detector electronics of the control device, a rapid serial configuration of the electronics units is possible, in particular within a few hundreds of milliseconds, specifically less than one second, possibly also less than 100 ms if a high clock speed is used, for example, in the range from 100 to 150 MHz. Therein, for example, a so-called serial slave channel is used, which is already available in many electronics components that can be utilized, for example FPGAs. Therefore a rapid configuration capability is specifically aimed for, in order to keep heating and/or control outages as short as possible. In particular, in comparison with previously used configuration initialization techniques which last, for example for 30 s to 60 s, a significant improvement is achieved with such a serial communication line and a restriction of a deactivation to the actual configuration timespan.

In concrete terms, as the regulating unit, an FPGA (field programmable gate array) can be used. FPGAs are often available with a configuration interface for a serial configuration line. With regard to the coordination of the new configuration and/or reconfiguration process, the control device can specifically use a control circuit and/or a microcontroller. This is then configured accordingly to continue operating the conditioning unit and only briefly to switch off the heating unit and/or continue to operate it constantly, that is under control, while the regulating unit is being newly configured and/or reconfigured. Further measures, as described below, can easily be implemented by a control circuit of this type and/or a microcontroller of this type.

It should therein be noted at this point that switchable power supply units are associated with the electronics units and/or the conditioning unit and/or the heating unit by a switch controllable via the control device, in particular a control circuit and/or a microcontroller.

As has already been mentioned, further heat sources which provide for a substantially constant heat input into the sensor material can also exist. For such a case, these heat sources can also be included in the operating concept described here in reconfiguration and/or new configuration processes.

A suitable development of embodiments of the present invention therefore provides that the control device also comprises a further electronics unit attached to the sensor material, emitting its heat loss directly to the sensor material, wherein by way of the control device, when a new configuration and/or reconfiguration takes place, the operation of the further electronics unit is also maintained. The further electronics unit can therein be, in particular, a measuring unit for detector signals and/or the further electronics unit can be designed as an application-specific integrated circuit (ASIC). Such measuring units can serve, in particular, for the readout and possibly already at least partial evaluation of detector signals which relate to the incidence of X-ray quanta onto the sensor material. The provision of such measuring units which cause a heat input into the sensor material by way of their heat loss is also maintained by a corresponding circuit measure during the reconfiguration and/or new configuration process, so that the at least one measuring unit and/or generally further electronics unit remains active continuously. A continuous heat input from the dissipation power into the sensor material therefore takes place, so that a contribution to keeping its temperature constant continues to be made.

As the sensor material, cadmium telluride (CdTe) and/or cadmium zinc telluride (CdZnTe) can preferably be used. These materials have proved to be extremely advantageous, in particular for medical imaging applications. Therefore, it can also suitably be provided that the X-ray detector is used in an imaging, in particular medical, X-ray device. The X-ray detector is preferably operated as a counting X-ray detector and therefore for recording and, in particular also energetic evaluation of, individual photon events.

Alongside the method, embodiments of the present invention also relate to a directly-converting X-ray detector, having:
   a directly-converting sensor material which is to be kept at a working temperature and to which a DC voltage is applied,
   a conditioning unit causing a base current to flow through the sensor material,
   a heating unit for the sensor material, regulated by a regulating unit to maintain the working temperature, and
   a control device having a plurality of electronics units comprising the regulating unit, wherein the control device is designed to carry out a method according to embodiments of the present invention. Finally, embodiments of the present invention also relate to an imaging X-ray device with an X-ray detector according to embodiments of the present invention. All the embodiments relating to the method according to embodiments of the present invention can be transferred similarly to the X-ray detector according to embodiments of the present invention and the X-ray device according to embodiments of the present invention, so that therewith the above-mentioned advantages can therefore also be achieved.

This means that in the context of embodiments of the present invention, circuit-related measures are provided, in particular, in the control circuit and/or the microcontroller, in order to ensure continued operation of heat-inputting units and/or the shortest possible interrupted or constant operation of the heating unit.

BRIEF DESCRIPTION OF THE DRAWINGS

Further advantages and details of the present invention are disclosed in the following description of exemplary embodiments and by reference to the drawings, in which.

DETAILED DESCRIPTION

Figure 1:
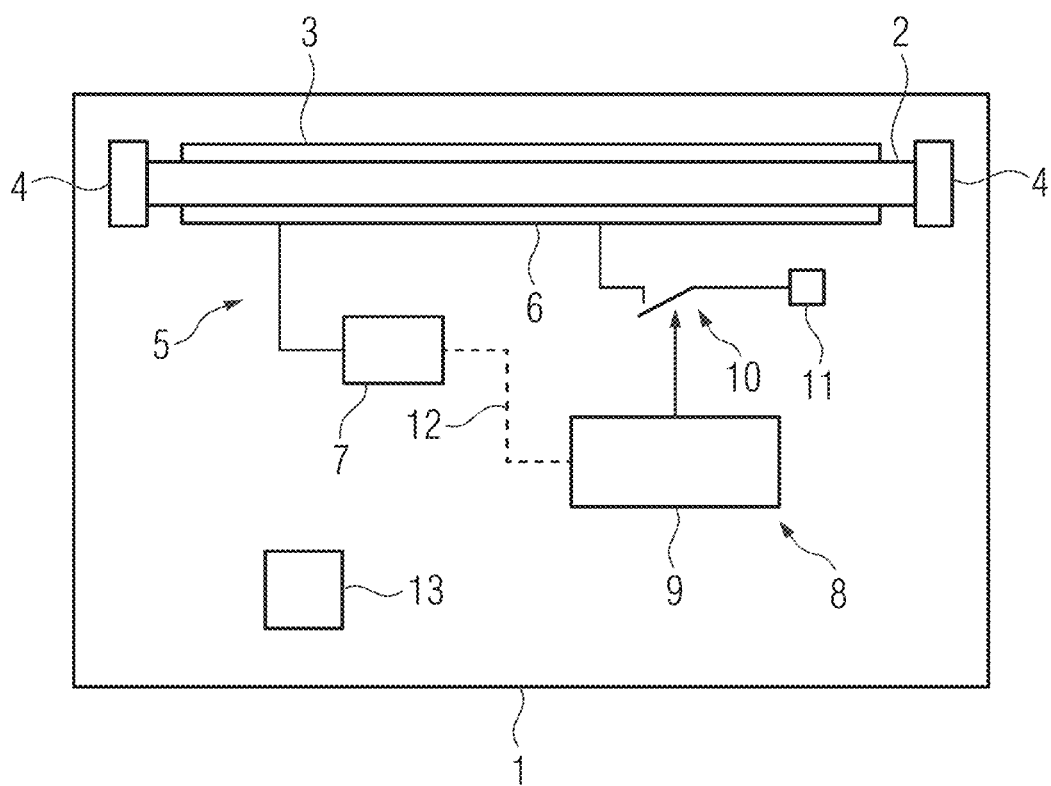
FIG. 1 is a schematic illustration of the structure of a directly-converting X-ray detector according to embodiments of the present invention.

FIG. 1 shows schematically the structure of a directly-converting, in this case, photon-counting X-ray detector 1 for the purpose of medical X-ray imaging, for example in a computed tomography device as the X-ray device.

The X-ray detector 1 utilizes a semiconductor sensor material 2, for example cadmium telluride and/or CZT, for direct conversion of X-ray photons into electric charge carriers which, on the basis of a DC voltage, in particular a high voltage, applied to it, for which a high voltage unit (not shown) is provided, generate a current which can be recorded as the detector signal of measuring units 4 designed here as ASICs. By way of the use of a conditioning unit 3 which, for example, can irradiate the sensor material, a certain base current flows through the sensor material 2 which provides for a certain amount of heating. By way of example, thereby a heating power in the range of 5 to 12 Watt can result. Further heating takes place due to the directly connected measuring units 4 by way of the heat loss which can pass by heat conduction into the sensor material 2. Herein, the heating power can be, for example, in the region of 1 to 5 Watt.

Since, however, the sensor material 2 exhibits unwanted drift effects as a result of temperature differences, it should be held at a predetermined working temperature, for which reason a sensor material heating device 5 is provided which comprises a heating unit 6 and a regulating unit 7 which drives the heating unit 6 such that it is regulated to the working temperature. Herein, temperature data from temperature sensors (not shown for the sake of clarity) can be used as measurement variables.

The conditioning unit 3, the measuring units 4 and the regulating unit 7 represent at least a portion of electronics units of a control device 8 of the X-ray detector 1 which also has a control circuit 9 and/or a microcontroller. In addition, switches 10 are associated with the heating unit 6, the conditioning unit 3 and the measuring units 4 for separating them from their power supply 11 and are controllable by the control device 8, in this case the control circuit 9, as shown, for the sake of clarity, only for the heating unit 6.

The control device 8 is configured to carry out the method according to embodiments of the present invention in order also to keep the temperature of the sensor material 2 as accurately as possible at the working temperature, even during the reconfiguration and new configuration processes. An exemplary embodiment of the method according to the present invention will now be described in more detail making reference to FIG. 2. This method sequence is implemented with technical circuit measures in the control device 8.

Figure 2:
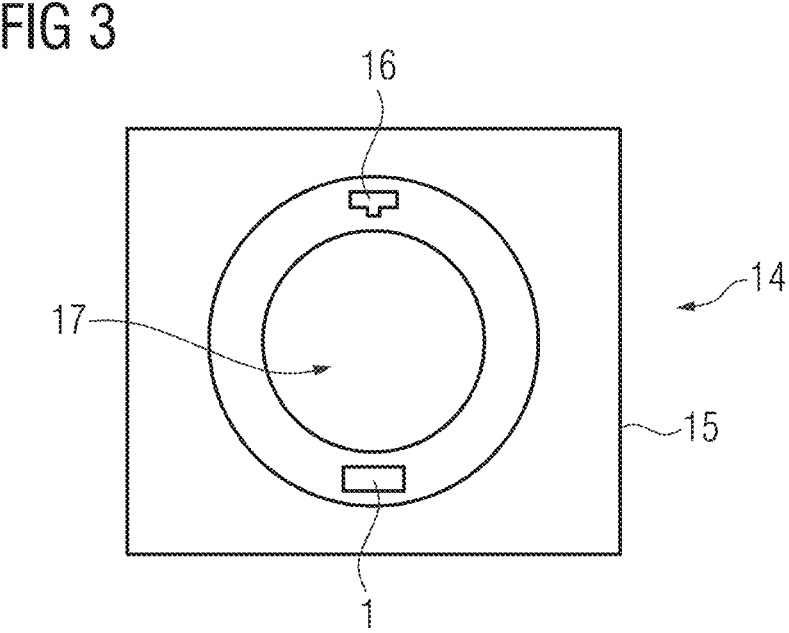
FIG. 2 is a flow diagram of an exemplary embodiment of the method according to the present invention.

If it is ascertained, in FIG. 2 by the control device 8 in a step S1, that currently a reconfiguration or new configuration process is taking place, then firstly in a step S2, regardless of other processes, the power supply for the conditioning unit 3 and the measuring unit 4 is maintained so that they remain active and provide their contribution to the heat input into the sensor material 2. At the same time, the power supply 11 for the regulating unit 7 and the heating unit 6 is initially maintained until it is available in step S3 for the new configuration and/or reconfiguration.

Then, in step S3 in the present exemplary embodiment, the heating unit 6 is deactivated by actuating the switch 10 only for as long as the configuration of the regulating unit 7 takes, that is, for a configuration period. In the present case, this is selected to be extremely short since the configuration takes place via a serial configuration line 12 (see FIG. 1), in particular with a high clock frequency. This results in configuration periods that are shorter than one second. As soon as this rapid reconfiguration or new configuration is completed, the regulating unit 7 and the heating unit 6 are put back into operation.

In order to provide for a frictionless transition, it can also be provided in this regard that the last control value is stored in a storage 13 of the control device 8 and when the operation of the regulating unit 7 is resumed, is utilized as the starting value. In some embodiments, it is also possible that the heating unit 6 is further operated by the control device 8, although constantly with the last control value ascertained during normal operation of the regulating unit 7. In each case, an unregulated operation of the heating unit 6 is prevented.

Figure 3:
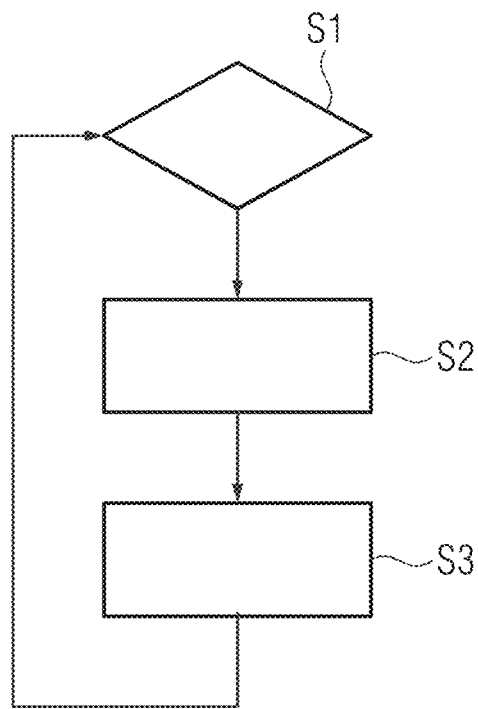
FIG. 3 is an X-ray system according to embodiments of the present invention.

Finally, FIG. 3 shows a sketch of the principle of an X-ray device 14, in this case a computed tomography device. This has, as known in principle, a gantry 15 in which an X-ray source 16 and an X-ray detector 1 as described by reference to FIG. 1 and FIG. 2 are arranged opposite one another.

Via a patient support (not shown), a patient can be moved into a field of view within a patient receiving region 17.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "on," "connected," "engaged," "interfaced," and "coupled." Unless explicitly described as being "direct," when a relationship between first and second elements is described in the disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" on, connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "example" is intended to refer to an example or illustration.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

It is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed above. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments. The present invention may, however, be embodied in many alternate forms and should not be construed as limited to only the embodiments set forth herein.

In addition, or alternative, to that discussed above, units and/or devices according to one or more example embodiments may be implemented using hardware, software, and/or a combination thereof. For example, hardware devices may be implemented using processing circuitry such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion. In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CD-ROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one example embodiment relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

Although the present invention has been illustrated and described in detail with regard to exemplary embodiments, the present invention is not restricted by the examples disclosed and other variations can be derived therefrom by a person skilled in the art without departing from the protective scope of the present invention.

What is claimed is:

1. A method of operating a directly-converting X-ray detector, the directly-converting X-ray detector including a directly-converting sensor material, a conditioning unit, a heating unit and a control device, the directly-converting sensor material being configured to have a DC voltage applied thereto, the conditioning unit being configured to cause a base current to flow through the directly-converting sensor material, the heating unit configured to be regulated by a regulating unit to maintain a working temperature of the directly-converting sensor material, the control device including the regulating unit, and the method being performed when at least one of a new configuration or a reconfiguration process is performed, the method comprises:
   maintaining operation of the conditioning unit;
   configuring the regulating unit via a serial configuration line, the serial configuration line being connected to a configuration interface of the regulating unit; and
   performing a first control operation of the heating unit only during an actual configuration time of the regulating unit, the first control operation including at least one of,
      interrupting operation of the heating unit, or
      maintaining the operation of the heating unit with a last ascertained control value, the last ascertained control value being a control value most recently ascertained in ordinary operation of the regulating unit.

2. The method as claimed in claim 1, further comprising:
   storing the last ascertained control value in a storage at the control device; and
   using the last ascertained control value as a starting value for the control value upon restart of ordinary operation of the regulating unit, the restart of ordinary operation of the regulating unit being after the actual configuration time.

3. The method as claimed in claim 2, wherein at least one of:
   the regulating unit is an FPGA; or
   the control device is configured to use at least one of a control circuit or a microcontroller to coordinate the at least one of the new configuration or the reconfiguration process.

4. The method as claimed in claim 2, wherein
   the control device includes an electronics unit directly attached to the directly-converting sensor material, the electronics unit being configured to emit heat loss to the directly-converting sensor material; and
   the method further comprises maintaining, by way of the control device, operation of the electronics unit when the at least one of the new configuration or the reconfiguration process takes place.

5. The method as claimed in claim 2, wherein at least one of:
   the actual configuration time is less than a second; or
   the directly-converting X-ray detector is a photon-counting detector.

6. The method as claimed in claim 1, wherein at least one of:
   the regulating unit is an FPGA; or
   the control device is configured to use at least one of a control circuit or a microcontroller to coordinate the at least one of the new configuration or the reconfiguration process.

7. The method as claimed in claim 6, wherein
   the control device includes an electronics unit directly attached to the directly-converting sensor material, the electronics unit being configured to emit heat loss to the directly-converting sensor material; and the method further comprises maintaining, by way of the control device, operation of the electronics unit when the at least one of the new configuration or the reconfiguration process takes place.

8. The method as claimed in claim 1, wherein
the control device includes an electronics unit directly attached to the directly-converting sensor material, the electronics unit being configured to emit heat loss to the directly-converting sensor material; and
the method further comprises maintaining, by way of the control device, operation of the electronics unit when the at least one of the new configuration or the reconfiguration process takes place.

9. The method as claimed in claim 8, wherein at least one of:
the regulating unit is an FPGA; or
the control device is configured to use at least one of a control circuit or a microcontroller to coordinate the at least one of the new configuration or reconfiguration process.

10. The method as claimed in claim 8, wherein at least one of:
the actual configuration time is less than a second; or
the directly-converting X-ray detector is a photon-counting detector.

11. The method as claimed in claim 8, wherein at least one of:
the electronics unit is a measuring unit for detector signals; or
the electronics unit is an application-specific integrated circuit.

12. The method as claimed in claim 1, wherein at least one of:
the directly-converting sensor material includes at least one of cadmium telluride or cadmium zinc telluride; or
the directly-converting X-ray detector is used in an imaging X-ray device.

13. The method as claimed in claim 12, wherein
the control device includes an electronics unit directly attached to the directly-converting sensor material, the electronics unit being configured to emit heat loss to the directly-converting sensor material; and
the method further comprises maintaining, by way of the control device, operation of the electronics unit when the at least one of the new configuration or the reconfiguration process takes place.

14. The method as claimed in claim 12, wherein at least one of:
the actual configuration time is less than a second; or
the directly-converting X-ray detector is a photon-counting detector.

15. The method as claimed in claim 1, wherein switchable power supplies are connected to at least one of the regulating unit, the conditioning unit or the heating unit via a switch, the switch being configured to be actuated by the control device.

16. The method as claimed in claim 1, wherein at least one of:
the actual configuration time is less than a second; or
the directly-converting X-ray detector is a photon-counting detector.

17. An X-ray detector, comprising:
a directly-converting sensor material configured to have a DC voltage applied thereto;
a conditioning unit configured to cause a base current to flow through the directly-converting sensor material;
a heating unit configured to be regulated by a regulating unit to maintain a working temperature of the directly-converting sensor material; and
a control device including the regulating unit, the control device being configured to carry out the method as claimed in claim 1.

18. The method as claimed in claim 17, further comprising:
ascertaining, by the control device, that the at least one of the new configuration or the reconfiguration process is being performed,
wherein the maintaining, the configuring and the performing are performed in response to the ascertaining.

19. An X-ray apparatus having the directly-converting X-ray detector as claimed in claim 17.

20. The method as claimed in claim 1, further comprising:
ascertaining that the at least one of the new configuration or the reconfiguration process is being performed,
wherein the maintaining, the configuring and the performing are performed in response to the ascertaining.

* * * * *